(12) United States Patent
Eom et al.

(10) Patent No.: US 11,607,147 B2
(45) Date of Patent: Mar. 21, 2023

(54) COMPONENT ANALYZING APPARATUS AND COMPONENT ANALYZING METHOD, AND IMPEDANCE MEASURING APPARATUS

(71) Applicant: SAMSUNG ELECTRONICS CO., LTD., Suwon-si (KR)

(72) Inventors: Kun Sun Eom, Yongin-si (KR); Sung Hyun Nam, Yongin-si (KR); Moon Seong Park, Suwon-si (KR); Yun S Park, Suwon-si (KR); Myoung Hoon Jung, Bucheon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 304 days.

(21) Appl. No.: 16/878,192

(22) Filed: May 19, 2020

(65) Prior Publication Data
US 2021/0219864 A1     Jul. 22, 2021

(30) Foreign Application Priority Data
Jan. 16, 2020   (KR) .................. 10-2020-0006139

(51) Int. Cl.
*A61B 5/0537*      (2021.01)
*A61B 5/0531*      (2021.01)
(Continued)

(52) U.S. Cl.
CPC .......... *A61B 5/0537* (2013.01); *A61B 5/0531* (2013.01); *A61B 5/14532* (2013.01);
(Continued)

(58) Field of Classification Search
CPC . A61B 5/0537; A61B 5/0531; A61B 5/14532; A61B 5/14546; A61B 5/6844; A61B 2562/043; A61B 5/053
See application file for complete search history.

(56) References Cited

U.S. PATENT DOCUMENTS 5,512,836 A * 4/1996 Chen .................... H03K 17/955
                                                           361/278
9,060,700 B2    6/2015 Cho et al.
(Continued)

FOREIGN PATENT DOCUMENTS

JP       2009-11555 A      1/2009
JP       4392279 B2       12/2009
(Continued)

OTHER PUBLICATIONS

Sanchez, B., Pacheck, A. & Rutkove, S. Guidelines to electrode positioning for human and animal electrical impedance myography research. Sci Rep 6, 32615 (2016). https://doi.org/10.1038/srep32615 (Year: 2016).*

(Continued)

*Primary Examiner* — Christian Jang
*Assistant Examiner* — Clarissa Cuevas
(74) *Attorney, Agent, or Firm* — Sughrue Mion, PLLC (57) ABSTRACT

A component analyzing apparatus is provided. The component analyzing apparatus includes: an impedance measurer including: a plurality of electrodes having an electrode width that is determined based on an effective measurement depth for analyzing a component of an analyte and a gap between two electrodes among the plurality of electrodes, and an electrode controller configured to apply a first current to a first electrode and a second electrode among the plurality of electrodes and configured to measure impedance based on a voltage between a third electrode and a fourth electrode; and a processor configured to analyze the component of the analyte based on the impedance measured by the electrode controller.

24 Claims, 9 Drawing Sheets

(51) Int. Cl.
*A61B 5/145* (2006.01)
*A61B 5/00* (2006.01)

(52) U.S. Cl.
CPC ........ *A61B 5/14546* (2013.01); *A61B 5/6844* (2013.01); *A61B 2562/043* (2013.01)

(56) References Cited

U.S. PATENT DOCUMENTS

| | | | |
|---|---|---|---|
| 9,213,010 | B2 | 12/2015 | Yang et al. |
| 9,357,958 | B2 | 6/2016 | Yang et al. |
| 9,408,567 | B2 | 8/2016 | Wang et al. |
| 9,625,414 | B2 | 4/2017 | Yang et al. |
| 9,625,415 | B2 | 4/2017 | Yang et al. |
| 9,632,060 | B2 | 4/2017 | Shah et al. |
| 9,645,111 | B2 | 5/2017 | Szyman et al. |
| 9,801,576 | B2 | 10/2017 | Yang et al. |
| 9,808,191 | B2 | 11/2017 | Yang et al. |
| 9,833,178 | B2 | 12/2017 | Aberg et al. |
| 9,861,746 | B2 | 1/2018 | Gautham et al. |
| 9,863,911 | B2 | 1/2018 | Wang et al. |
| 9,989,490 | B2 | 6/2018 | Yang et al. |
| 9,989,491 | B2 | 6/2018 | Szyman et al. |
| 10,156,543 | B2 | 12/2018 | Yang et al. |
| 10,172,544 | B2 | 1/2019 | Yang et al. |
| 10,321,865 | B2 | 6/2019 | Gautham et al. |
| 10,335,076 | B2 | 7/2019 | Wang et al. |
| 10,335,077 | B2 | 7/2019 | Wang et al. |
| 10,342,468 | B2 | 7/2019 | Wang et al. |
| 2005/0090760 | A1 | 4/2005 | Kobayashi |
| 2007/0265512 | A1 | 11/2007 | Ollmar et al. |
| 2010/0130883 | A1 | 5/2010 | Carpenter et al. |
| 2013/0331674 | A1 | 12/2013 | Yang et al. |
| 2013/0331676 | A1 | 12/2013 | Morgan et al. |
| 2014/0046156 | A1 | 2/2014 | Hayter et al. |
| 2015/0073242 | A1 | 3/2015 | Sokolov et al. |
| 2016/0113540 | A1* | 4/2016 | Chi ............... A61B 5/276 600/509 |
| 2016/0135741 | A1* | 5/2016 | Chetham ............. A61B 5/08 600/391 |
| 2016/0320338 | A1 | 11/2016 | Wang et al. |
| 2017/0164879 | A1 | 6/2017 | Yang et al. |
| 2019/0034594 | A1* | 1/2019 | DiPerna ............... G16H 40/60 |
| 2019/0059793 | A1 | 2/2019 | Yang et al. |
| 2019/0059794 | A1 | 2/2019 | Yang et al. |
| 2019/0060556 | A1* | 2/2019 | Huiszoon ............... A61B 5/20 |
| 2019/0076068 | A1 | 3/2019 | Yang et al. |
| 2019/0183726 | A1 | 6/2019 | McCanny et al. |
| 2019/0200883 | A1 | 7/2019 | Moon et al. |
| 2019/0269355 | A1 | 9/2019 | Wang et al. |

FOREIGN PATENT DOCUMENTS

| | | |
|---|---|---|
| JP | 5626049 B2 | 11/2014 |
| JP | 2016-55059 A | 4/2016 |
| JP | 2017-538474 A | 12/2017 |
| JP | 2018-139761 A | 9/2018 |
| KR | 10-1737283 B1 | 5/2017 |
| KR | 10-2018-0036681 A | 4/2018 |
| KR | 10-2018-0097370 A | 8/2018 |

OTHER PUBLICATIONS

A. Caduff et al., "Dynamics of blood electrolytes in repeated hyper-and/or hypoglycaemic events in patients with type 1 diabetes", Diabetologia, 54, DOI 10.1007/s00125-011-2210-9, Jun. 15, 2011, pp. 2678-2689, 12 pages total.

Biff F. Palmer et al., "Electrolyte and Acid-Base Disturbances in Patients with Diabetes Mellitus", The New England Journal of Medicine, 373;6, DOI: 10.1056/NEJMra1503102, Aug. 6, 2015, pp. 548-559, 12 pages total.

K.-G. Petersen et al., "Glucose-induced water movement from the intracellular to the extracellular space and its influence on calculations of glucose metabolism", European Journal of Clinical Investigation, 23, 1993, pp. 266-269, 4 pages total.

Teresa A. Hillier et al., "Hyponatremia: Evaluating the Correction Factor for Hyperglycemia", The American Journal of Medicine, vol. 106, Apr. 1999, pp. 399-403, 5 pages total.

\* cited by examiner

COMPONENT ANALYZING APPARATUS AND COMPONENT ANALYZING METHOD, AND IMPEDANCE MEASURING APPARATUS

CROSS-REFERENCE TO RELATED APPLICATION(S)

This application claims priority from Korean Patent Application No. 10-2020-0006139, filed on Jan. 16, 2020, in the Korean Intellectual Property Office, the entire disclosure of which is herein incorporated by reference for all purposes.

BACKGROUND

1. Field

Example embodiments relate to a component analyzing apparatus and a component analyzing method for analyzing a component of an analyte by using bio-impedance, and an impedance measuring apparatus.

2. Description of Related Art

Various medical devices are being developed for diagnosis of health conditions of patients. The importance of medical devices for measuring electric bio-signals of patients in medical examinations is emphasized to improve patient's convenience and to provide speedy medical examination results. Particularly, bio-impedance may be used to monitor physical or emotional conditions of a human body, and studies have been conducted to manufacture small devices for measuring bio-impedance, and to provide methods of rapidly and accurately measuring the bio-impedance.

SUMMARY

In an accordance with an aspect of an example embodiment, there is provided a component analyzing apparatus, including: an impedance measurer including: a plurality of electrodes having an electrode width that is determined based on an effective measurement depth for analyzing a component of an analyte and a gap between two electrodes among the plurality of electrodes, and an electrode controller configured to apply a first current to a first electrode and a second electrode among the plurality of electrodes and configured to measure impedance based on a voltage between a third electrode and a fourth electrode; and a processor configured to analyze the component of the analyte based on the impedance measured by the electrode controller.

The plurality of electrodes may be arranged in a Wenner array or in a Wenner-Schlumberger array.

The plurality of electrodes may be arranged in a Wenner array, and the electrode width may be predetermined by using a model that defines a correlation between a ratio between an electrode width and a gap of adjacent electrodes, and an effective measurement depth.

The plurality of electrodes may be arranged in a Wenner-Schlumberger array, and the electrode width may be predetermined by using a model that defines a correlation between a ratio between an electrode width and a separation factor, and an effective measurement depth.

The analyte may include dermis of an object.

The processor may be further configured to control the electrode controller to monitor a contact state between the plurality of electrodes and an object by measuring, in a fasting state of a user, a plurality of impedance values in the contact state, and the processor may be further configured to determine whether a contact position of the plurality of electrodes with respect to the object is acceptable based on the measured plurality of impedance values.

The processor may be further configured to obtain an impedance deviation based on the measured plurality of impedance values, and provide information to the user to change the contact position based on the impedance deviation being greater than a predetermined threshold value.

The processor may be further configured to, based on a request for component analysis, provide information on the contact position that is determined as acceptable.

The processor may be further configured to control the electrode controller to apply a second current to a fifth electrode and a sixth electrode among the plurality of electrodes, and measure the plurality of impedance values by measuring voltages between the third electrode and the fourth electrode.

A gap between the fifth electrode and the sixth electrode may be narrower than a gap between the first electrode and the second electrode.

The gap between the fifth electrode and the sixth electrode may be within a predetermined multiple of a gap between the third electrode and the fourth electrode.

The processor may be further configured to control the electrode controller to monitor the contact state by applying a third current to the first electrode and the second electrode, and measuring the plurality of impedance values based on voltages between the third electrode and the fourth electrode.

The processor may be further configured to, based on a request for component analysis, control the electrode controller to monitor a contact state between the plurality of electrodes and an object by measuring a plurality of impedance values, and measure the impedance for component analysis based on the monitored contact state being acceptable.

The component of the analyte may include at least one of blood glucose, cholesterol, triglyceride, protein, intracellular water, extracellular water, body water, and uric acid.

In an accordance with an aspect of an example embodiment, there is provided a component analyzing method, including: applying a first current to a first electrode and a second electrode among a plurality of electrodes, the plurality of electrodes having an electrode width determined based on an effective measurement depth for analyzing a component of an analyte and a gap between two electrodes among the plurality of electrodes; measuring impedance based on a voltage between a third electrode and a fourth electrode among the plurality of electrodes; and analyzing the component of the analyte based on the measured impedance.

The analyte may include dermis of an object.

The method may further include monitoring a contact state between the plurality of electrodes and an object by measuring, in a fasting state of a user, a plurality of impedance values in the contact state; and determining whether a contact position of the plurality of electrodes with respect to the object is acceptable based on the measured plurality of impedance values.

The determining may include obtaining an impedance deviation based on the measured plurality of impedance values; and providing information to the user to change the contact position based on the impedance deviation being greater than a predetermined threshold value.

The method may further include, based on a request for component analysis, providing information on the contact position that is determined as acceptable.

The monitoring may include applying a second current to a fifth electrode and a sixth electrode among the plurality of electrodes; and measuring the plurality of impedance values based on voltages between the third electrode and the fourth electrode.

A gap between the fifth electrode and the sixth electrode may be narrower than a gap between the first electrode and the second electrode.

The monitoring may include applying a third current to the first electrode and the second electrode; and measuring the plurality of impedance values by based on voltages between the third electrode and the fourth electrode.

In an accordance with an aspect of an example embodiment, there is provided an impedance measuring apparatus, including: a plurality of electrodes having an electrode width determined based on an effective measurement depth for analyzing a component of an analyte and a gap between two electrodes among the plurality of electrodes; and an electrode controller configured to apply a current to a pair of current electrodes among the plurality of electrodes, and configured to measure impedance based on a voltage between a pair of voltage electrodes among the plurality of electrodes.

The electrode controller may be further configured to determine the electrode width by using a model that defines a correlation between a gap between two electrodes, an electrode width, and an effective measurement depth.

BRIEF DESCRIPTION OF THE DRAWINGS

The above and/or other aspects and features of certain example embodiments will be more apparent from the following description taken in conjunction with the accompanying drawings, in which.

DETAILED DESCRIPTION

Details of other example embodiments are included in the following detailed description and drawings. Advantages and features of the disclosure, and methods of achieving the same will be more clearly understood from the following example embodiments described in detail with reference to the accompanying drawings. Throughout the drawings and the detailed description, unless otherwise described, the same drawing reference numerals will be understood to refer to the same elements, features, and structures. The relative size and depiction of these elements may be exaggerated for clarity, illustration, and convenience.

It will be understood that, although the terms first, second, etc. may be used herein to describe various elements, these elements should not be limited by these terms. These terms are only used to distinguish one element from another. Any references to singular may include plural unless expressly stated otherwise. In addition, unless explicitly described to the contrary, an expression such as "comprising" or "including" will be understood to imply the inclusion of stated elements but not the exclusion of any other elements. Also, the terms, such as 'part' or 'module', etc., should be understood as a unit that performs at least one function or operation and that may be embodied as hardware, software, or a combination thereof.

Hereinafter, example embodiments of a component analyzing apparatus and a component analyzing method will be described in detail with reference to the accompanying drawings. The example embodiments of the component analyzing apparatus may be mounted in a medical device used in specialized medical institutions, a wearable device such as a smart watch worn on a wrist, a smart band type wearable device, a headphone type wearable device, a headband type wearable device, and the like, or a mobile device such as a smartphone, a tablet personal computer (PC), and the like.

Figure 1:
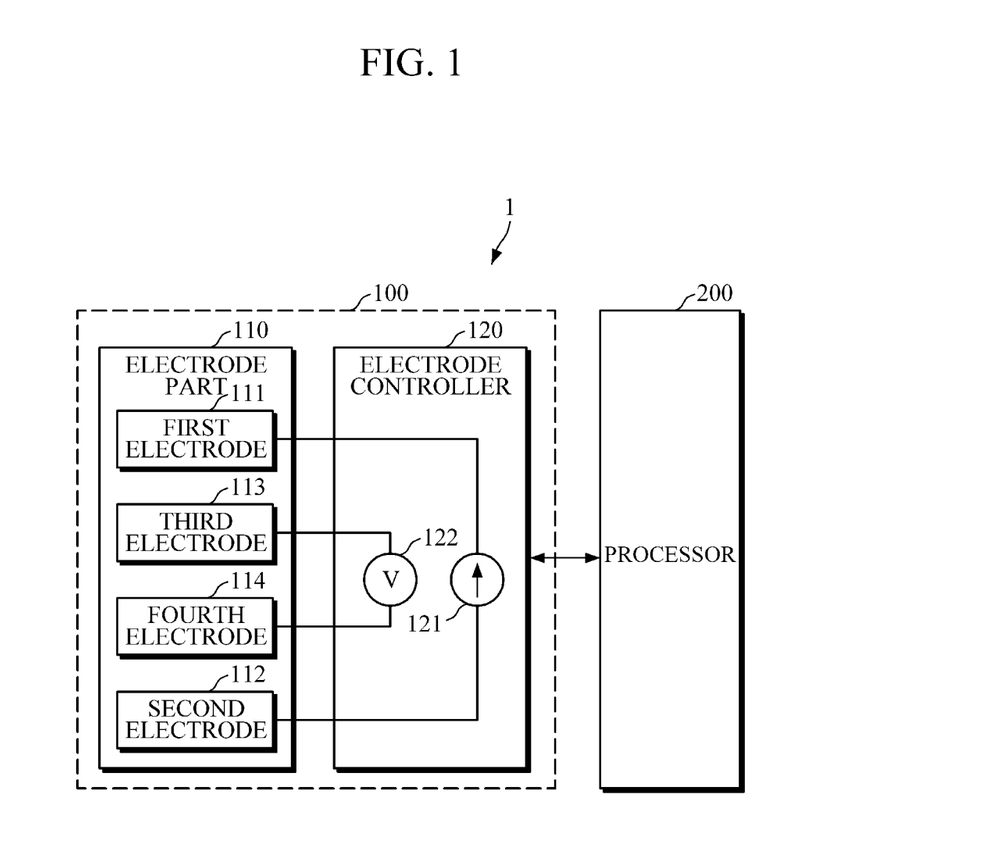
FIG. 1 is a block diagram illustrating a component analyzing apparatus according to an example embodiment.

FIG. 1 is a block diagram illustrating a component analyzing apparatus according to an example embodiment.

Referring to FIG. 1, a component analyzing apparatus 1 according to an example embodiment includes an impedance measurer 100 and a processor 200. The impedance measurer 100 and the processor 200 of the component analyzing apparatus 1 may be integrally formed in a single hardware device. However, the component analyzing apparatus 1 is not limited thereto, and the impedance measurer 100 may be formed as a single hardware device and the processor 200 may be mounted in, for example, a mobile device, separately from the impedance measurer 100, such that the impedance measurer 100 and the processor 200 may be electrically connected directly or via wired or wireless communications.

The impedance measurer 100 includes an electrode part 111 and an electrode controller 120.

The electrode part 110 includes a pair of a first electrode 111 and a second electrode 112, to which a current is applied, and a pair of a third electrode 113 and a fourth electrode 114 which measure a voltage applied to an analyte, which is generated by the current applied to the first electrode 111 and the second electrode 112. Accordingly, impedance may be measured using a four-electrode method.

The electrode controller 120 may apply a current to the first electrode 111 and the second electrode 112 of the electrode part 110, and may measure impedance by measuring a voltage applied to the third electrode 113 and the fourth electrode 114.

The electrode controller 120 may be electrically connected to the processor 200 or may be connected thereto via wireless communications, and may receive a control signal from the processor 200 and transmit the measured impedance to the processor 200.

The electrode part 110 includes a plurality of electrodes which are arranged in a predetermined shape. For example, the plurality of electrodes of the electrode part 111 may be arranged in a Wenner array or a Wenner-Schlumberger array.

A gap between the electrodes of the electrode part 110 may be predetermined, and may be set to, for example, 2 mm or less. Further, by considering an effective measurement depth for analyzing components of an analyte and/or an electrode gap, an optimal electrode width may be predetermined, and each electrode may be manufactured to have the determined optimal electrode width.

Figure 3:
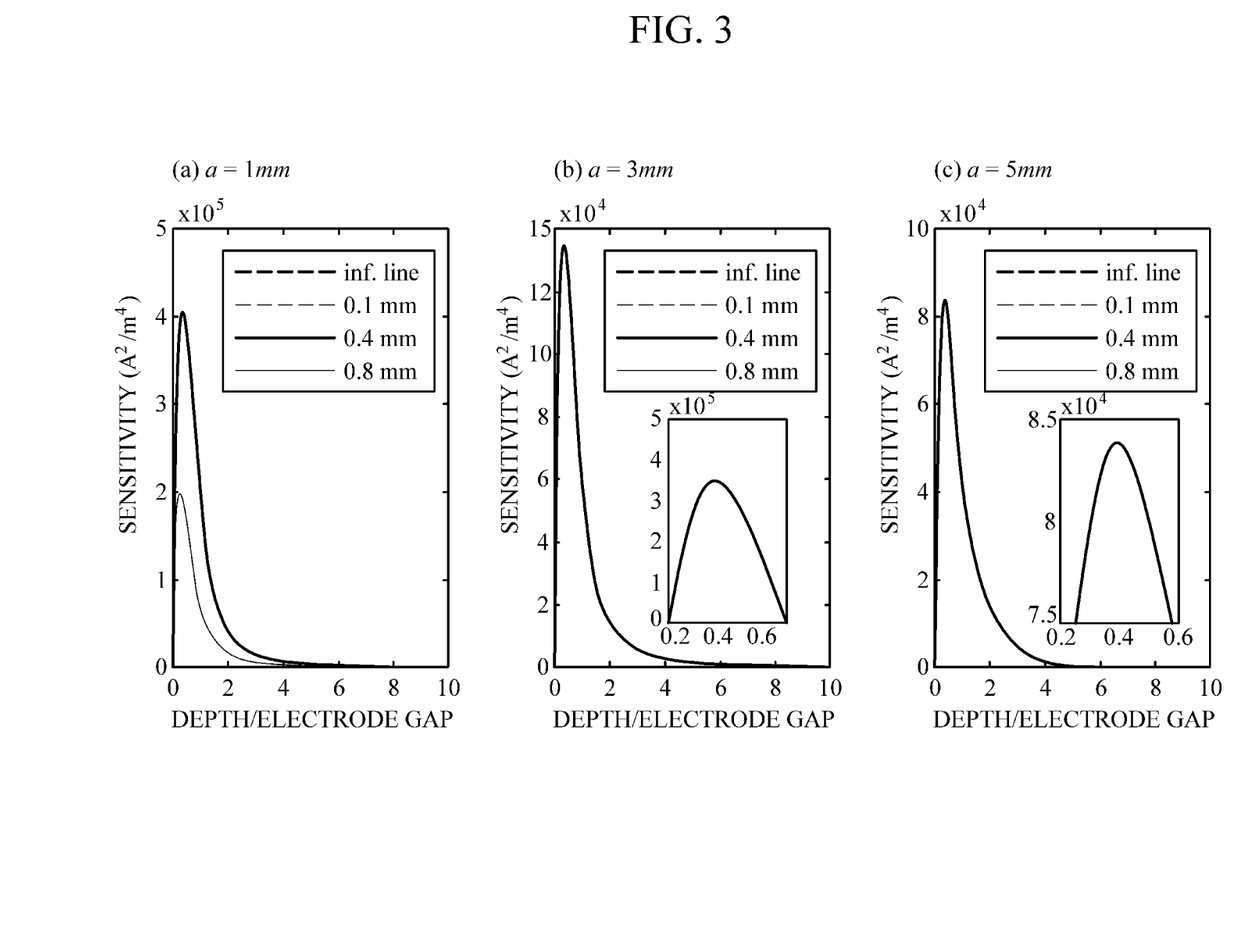
FIGS. 3, 4, and 5 are diagrams explaining methods of determining an electrode width of electrodes according to example embodiment.
Figure 4:
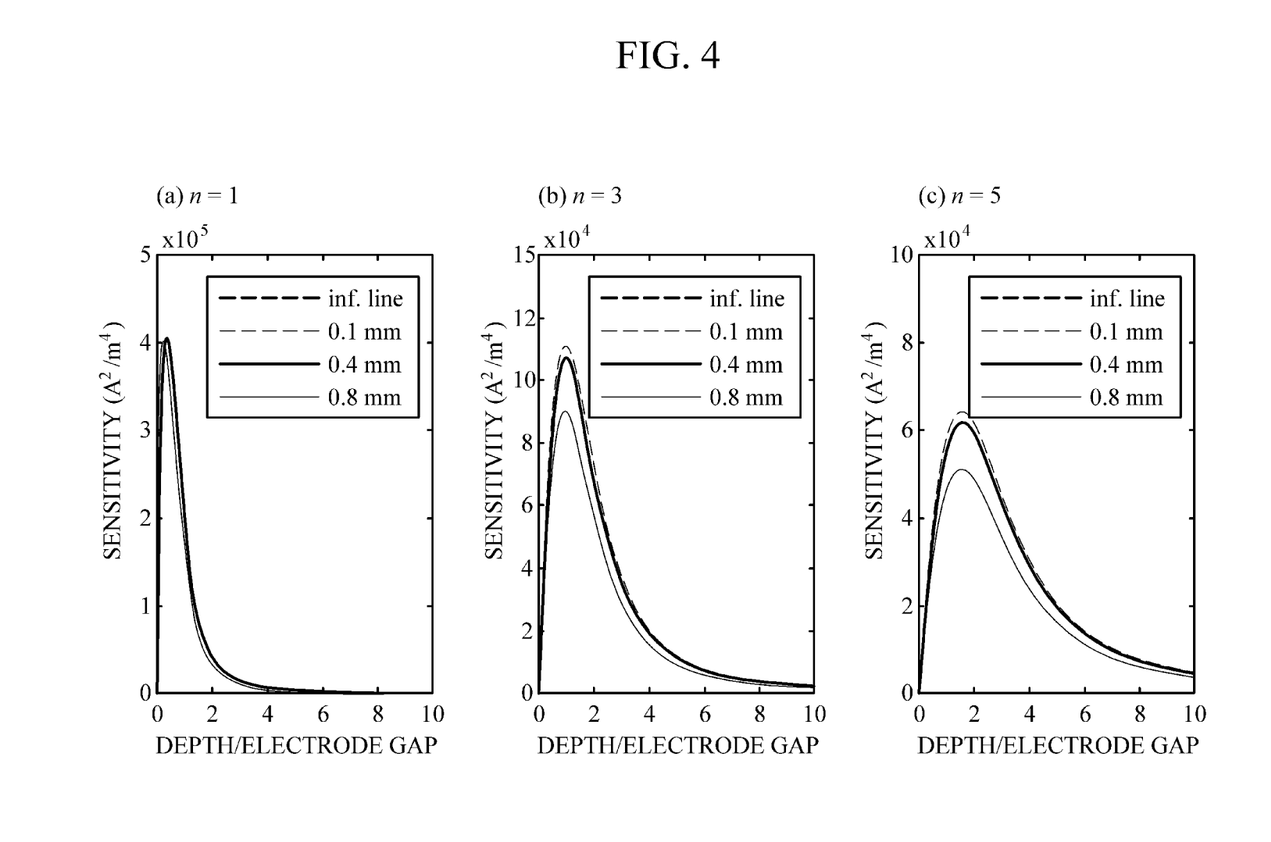
Figure 5:
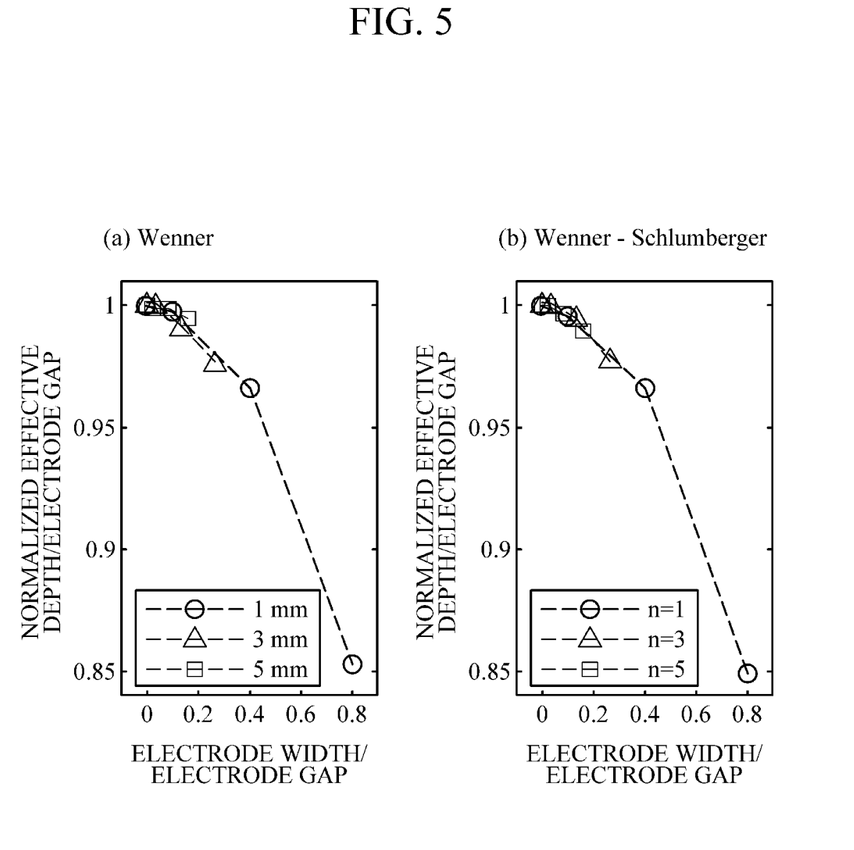

FIGS. 3, 4, and 5 are diagrams explaining methods of determining an optimal electrode width of electrodes.

Generally, electric impedance tomography is a non-destructive tomographic imaging technique using an electric field, and an effective measurement depth during the electric impedance tomographic imaging may vary depending on an electrode structure. FIG. 3 is a graph showing a change in sensitivity according to a change in an electrode width and an effective measurement depth in the Wenner electrode array, with respect to electrode gaps a of 1 mm ((a) of FIG. 3), 3 mm ((b) of FIG. 3), and 5 mm ((c) of FIG. 3). The sensitivity change is shown for each effective measurement depth for an infinite line electrode (inf. line) having an electrode width of 0, and for infinite surface electrodes having electrode widths of 0.1 mm, 0.4 mm, and 0.8 mm. The effective measurement depth $Z_{eff}$ may be determined by the following Equation 1. In Equation 1, sensitivity indicates a sensitivity level.

$$\frac{\int_0^{z_{eff}} \text{sensitivity } dz}{\int_0^{\infty} \text{sensitivity } dz} = 0.5 \qquad \text{[Equation 1]}$$

As illustrated in FIG. 3, as the electrode width increases, the sensitivity graph according to the depth is shifted towards a shallower depth, such that when electric impedance is measured, the effective measurement depth is reduced. Accordingly, an optimal electrode width for securing a desired effective measurement depth may be determined based on such a relationship, and the width of each electrode of the electrode part 110 may be adjusted at the time of manufacture, so that the electrodes may have the determined optimal electrode width, thereby improving accuracy of impedance measurement.

FIG. 4 is a graph showing a change in sensitivity according to a change in an electrode width in the Wenner-Schlumberger electrode array. The four-electrode Wenner-Schlumberger array is a linear array, in which when a gap between two inner electrodes among the four electrodes is defined as "a", a gap between two outer electrodes is determined to be "n×a". In this case, n is a separation factor.

As illustrated in FIG. 4, with respect to an electrode gap of 1 mm, and separation factors n of 1 ((a) of FIG. 4), 3 ((b) of FIG. 4), and 5 ((c) of FIG. 4), the sensitivity change is shown for each effective measurement depth for an infinite line electrode having an electrode width of 0, and infinite surface electrodes having electrode widths of 0.1 mm, 0.4 mm, and 0.8 mm. The effective measurement depth may be determined by using the above Equation 1. As in the Wenner electrode array, the sensitivity graph according to the depth in the Wenner-Schlumberger array is shifted towards a shallower depth as the electrode width increases, such that when electric impedance is measured, the effective measurement depth is reduced. Accordingly, an optimal electrode width for securing a desired effective measurement depth may be determined based on such a relationship.

FIG. 5 is a graph showing a change in sensitivity according to a change in an electrode width in the Wenner electrode array consisting of four electrodes ((a) of FIG. 5) and the Wenner-Schlumberger electrode array consisting of four electrodes ((b) of FIG. 5).

The impedance measurer 100 may determine an optimal electrode width by considering an effective measurement depth and an electrode gap (including a separation factor in the Wenner-Schlumberger electrode array) by preprocessing at the time of manufacture. Referring to (a) of FIG. 5, in the Wenner electrode array, a model for determining an electrode width may be generated, which defines a correlation between a ratio between an electrode width and an electrode gap between adjacent electrodes and a ratio between an effective measurement depth and an electrode gap. Referring to (b) of FIG. 5, in the Wenner-Schlumberger electrode array, a model for determining an electrode width may be generated, which defines a correlation between a ratio between an electrode width and a separation factor and a ratio between an effective measurement depth and an electrode gap.

By adjusting the electrode gap and the electrode width in consideration of various conditions such as the purpose of use of the impedance measurer 100, a component to be analyzed, the size of the impedance measurer 100, etc., the electrode controller 120 may determine an optimal electrode width for securing a desired effective measurement depth.

By performing the above preprocessing, the electrode controller 120 may generate the model for determining an electrode width, wherein the model defines a correlation between the effective measurement depth, the electrode gap, and the electrode width as shown in the graphs (a) and (b) of FIG. 5. By using the generated model for determining an electrode width, the electrode controller 120 may determine a proper electrode gap and an optimal electrode width according to the effective measurement depth for a component to be analyzed, a device in which the impedance measurer 120 is mounted, e.g., a wearable device such as a smart watch, and the like.

For example, (a) of FIG. 5 shows that when electrode gaps are 1 mm, 3 mm, and 5 mm in the four-electrode Wenner electrode array, the effective measurement depth decreases as the electrode width increases. For example, in the Wenner electrode array with an electrode gap of 5 mm, if impedance is measured for an effective measurement depth of 3 mm or less, an effective measurement depth/electrode gap before normalization in an infinite line electrode of the Wenner electrode array is generally 0.707, and a desired effective measurement depth/electrode gap is 0.6, such that when a normalized effective measurement depth/electrode gap in (a) is defined as 1, a normalized effective measurement depth/electrode gap is about 0.85. Accordingly, the electrode width/electrode gap, corresponding to 0.85, is about 0.8, such that the optical electrode width may be determined to be 4 mm.

Likewise, (b) of FIG. 5 shows that when an electrode gap is 1 mm and a separation factors n are 1, 3, and 5 in the four-electrode Wenner-Schlumberger electrode array, the effective measurement depth decreases as the electrode width increases. For example, in the Wenner-Schlumberger electrode array with an electrode gap of 1 mm and a separation factor of 3, if impedance is measured for an effective measurement depth of 1.75 mm or less, an effective measurement depth/electrode gap before normalization in an infinite line electrode of the Wenner-Schlumberger electrode array is generally 1.77, and a desired effective measurement depth/electrode gap is 1.75, such that when a normalized effective measurement depth/electrode gap in (a) is defined as 1, a normalized effective measurement depth/electrode gap is about 0.989, and an electrode width/separation factor is 0.188 at this time. Accordingly, an optimal electrode width may be determined to be 0.564 mm.

As described above, by adjusting an optimal electrode width to secure the effective measurement depth according to a component to be analyzed, and by manufacturing an impedance measuring apparatus to have the adjusted optimal electrode width, a desired effective measurement depth may be secured, thereby enabling accurate impedance measurement.

The processor 200 may control the electrode controller 120 to analyze a component or to monitor a contact state. Further, by using the impedance of an analyte, which is received from the electrode controller 120, the processor 200 may analyze a component of the analyte or may monitor a contact state of an electrode. The analyte may be dermis, but is not limited. Further, the component of the analyte may include blood glucose, cholesterol, triglyceride, protein, intracellular water, extracellular water, body water, uric acid, and the like, but is not limited thereto.

In addition, a channel may be formed at a main body substrate to store a fluid, so that impedance may be measured in vitro while flowing the fluid to be analyzed. In this case, the channel may include an inlet, through which the fluid is introduced, a storage, in which the introduced fluid is stored, and an outlet, through which the fluid is discharged. The fluid to be analyzed may be blood obtained invasively from an object, or may be a sample solution which mimics actual blood to have similar physical properties to those of blood.

Figure 6:
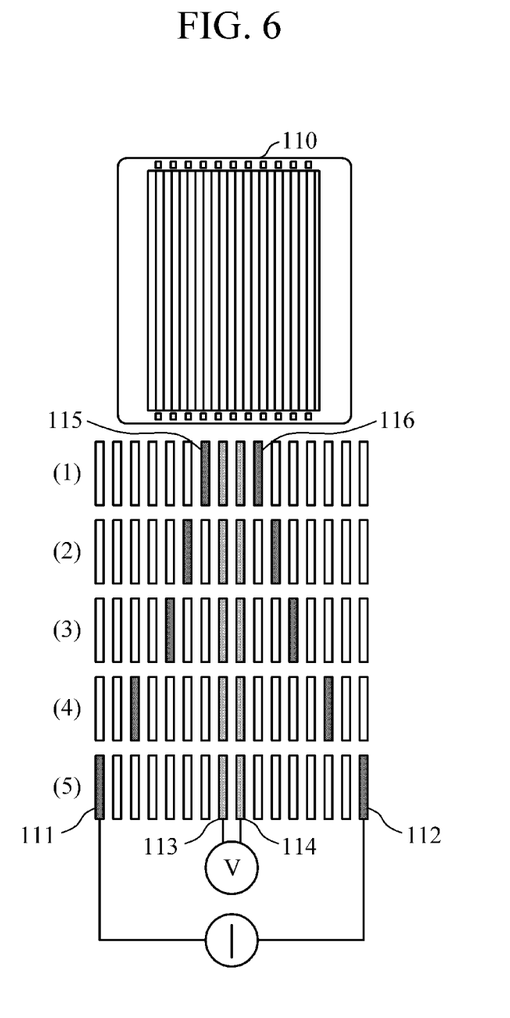
FIG. 6 is a diagram explaining an electrode part according to an example embodiment.

FIG. 6 is a diagram explaining an electrode part 110 according to an example embodiment.

For example, as illustrated in FIG. 6, if the electrode part 110 is arranged in a four-electrode Wenner-Schlumberger array, an effective measurement depth is 3 mm, and an electrode gap according to an optimal electrode width, i.e., a separation factor n, is determined to be 7, the electrode controller 120 may apply a current by driving a pair of outermost electrodes 111 and 112 as current electrodes, and may measure a voltage by driving a pair of innermost electrodes 113 and 114 as voltage electrodes, as illustrated in (5) of FIG. 6 in response to a request for measuring impedance required for the processor 200 to analyze a component. However, the electrode controller 120 is not limited thereto, and the opposite case is also possible. That is, the electrode controller 120 may also drive a pair of the innermost electrodes as current electrodes and a pair of the outermost electrodes as voltage electrodes.

In this case, two or more frequencies, including a frequency of 50 kHz or higher or less, may be used for the applied current. In an example embodiment, a gap between the current electrodes for component analysis may be equal to or greater than a predetermined multiple (e.g., approximately three times) of a gap between the voltage electrodes. By contrast, a gap between the voltage electrodes may be equal to or greater than a predetermined multiple (e.g., approximately three times) of a gap between the current electrodes.

Further, upon receiving a request for monitoring a contact state, the processor 200 may monitor a contact state between the electrode part 110 and an object. Alternatively, the processor 200 may be predetermined to monitor a contact state prior to analyzing a component, and upon receiving a request for component analysis, the processor 200 may monitor a contact state before performing component analysis, and may determine whether to perform component analysis based on the monitoring result. The processor 200 may monitor the contact state upon receiving a user's request, or at predetermined intervals, or if the processor 200 is predetermined to monitor a contact state prior to performing component analysis, or if the processor 200 determines that accuracy is lower based on a component analysis result according to predetermined criteria.

For example, when a user is at rest in a fasting state, the processor 200 may monitor a contact state between the electrode part 120 and the object, and may determine an optimal contact state (or determine whether the contact state is acceptable).

While the user is in a fasting state, the processor 200 may control the electrode controller 120 a predetermined number of times (e.g., three times) at predetermined time intervals (e.g., 15 minutes), to measure a plurality of impedance values for monitoring the contact state.

For example, referring to (5) of FIG. 6, the electrode controller 120 may measure a plurality of impedance values by using four electrodes, i.e., a first electrode 111, a second electrode 112, a third electrode 113, and a fourth electrode 114. In this case, current electrodes and voltage electrodes for measuring a component and current electrodes and voltage electrodes for monitoring a contact state may be shared.

In another example, referring to (1) of FIG. 6, the electrode controller 120 may measure the plurality of impedance values by driving a pair of electrodes 115 and 116 as current electrodes, separately from the current electrodes 111 and 112 for component analysis, and by driving a pair of innermost electrodes 113 and 114 as voltage electrodes. In this case, the current electrodes for monitoring a contact state are different from the current electrodes for analyzing a component, and the voltage electrodes are shared. In this case, a gap between the separate electrodes, i.e., the current electrodes, may be set to be equal to or less than a predetermined multiple (e.g., three times) of a gap between the voltage electrodes. Further, the separate current electrodes 115 and 116 may have a narrower gap than a gap between the current electrodes 111 and 112 for component analysis.

As described above, by measuring epidermis impedance by using separate electrodes having a narrow gap therebetween, and by monitoring the contact state by using the electrodes, an effect caused by a change in epidermis which forms a large part of the impedance in component analysis, e.g., an effect caused by an external environment such as a contact state, pressure, temperature, etc., may be minimized while an effective measurement depth increases with an increase in a separation factor.

Upon measuring the plurality of impedance values, the processor 200 may calculate a deviation (or variation) between the impedance values, and may compare the calculated deviation with a pre-defined threshold value. If the impedance deviation is greater than or equal to the threshold value, the processor 200 may determine that a contact state is abnormal, and may guide a user to change the contact state. In this case, the threshold value may be pre-defined, and may be set differently, for example, depending on whether using current electrodes (e.g., 4%) for estimating a component or using separate current electrodes (e.g., 5%). In this case, the processor 200 may determine a level of change of the contact state based on a difference between the impedance deviation and the threshold value.

If the calculated impedance deviation is less than a predetermined threshold value, the processor 200 may determine that a contact state is normal, and may determine a current contact position to be an optimal contact position (or acceptable) and store the contact position.

Then, upon receiving a request for component analysis, the processor 200 may provide guide information on the determined optimal contact position for a user. Once the user changes a position of the electrode part 110 to the optimal contact position according to the guide information, the processor 200 may control the electrode controller 120 to measure impedance in the optimal contact position.

In another example, upon receiving the request for component analysis, the processor 200 may monitor a contact state before measuring the impedance for component analysis. Upon receiving the request for component analysis, the processor 200 may control the electrode controller 120 at predetermined time intervals to measure a plurality of impedance values, and may monitor a contact state based on the measured impedance values. The monitoring of the contact state may be performed in the manner described above.

If the contact state is determined to be normal based on the monitoring result of the contact state, the processor 200 may control the electrode controller 120 to measure impedance for component analysis. By contrast, if the contact state is not determined to be normal based on the monitoring result of the contact state, the processor 200 may guide a user to change a contact position, and once the user changes the contact position, the processor 200 may control the electrode controller 120 to re-measure a plurality of impedances for monitoring a contact state.

The processor 200 may analyze a component of an analyte based on the impedance measured in a normal contact position according to the guide information on the optimal contact position determined in a fasting state, or in response to a request for component analysis. For example, by applying a component analysis model which defines a correlation between the impedance and the component, the processor 200 may obtain an estimated component value from the measured impedance. The component analysis model may be expressed in the form of a linear function, but is not limited thereto, and may be defined by various methods such as linear/nonlinear regression analysis, neural network, deep learning, and the like.

Figure 2:
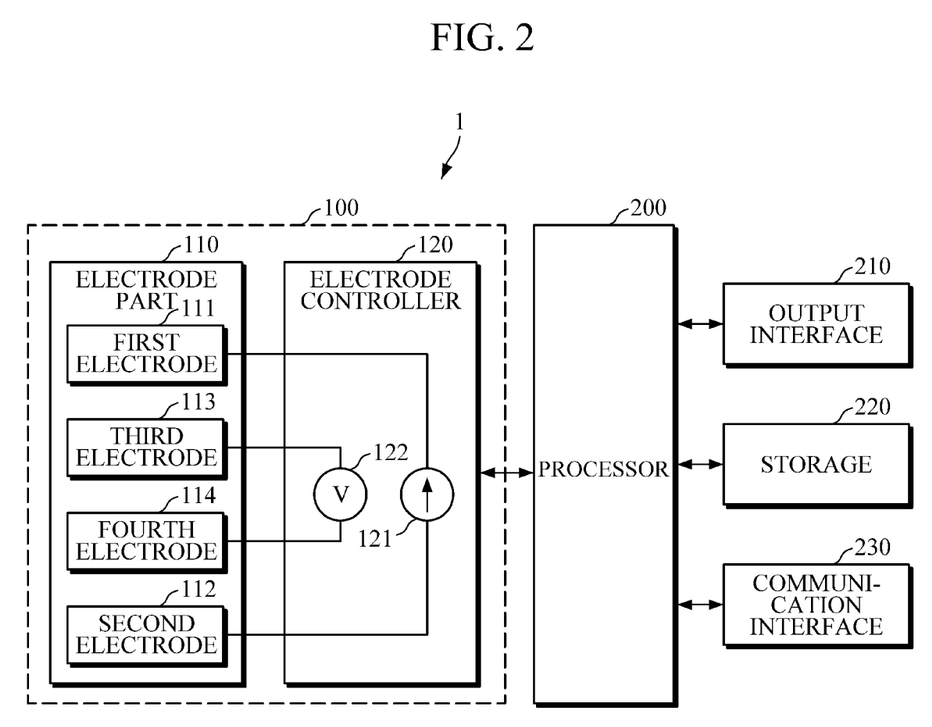
FIG. 2 is a block diagram illustrating a component analyzing apparatus according to another example embodiment.

FIG. 2 is a block diagram illustrating a component analyzing apparatus according to another example embodiment.

Referring to FIG. 2, the component analyzing apparatus 1 according to another example embodiment includes the impedance measurer 100, the processor 200, an output interface 210, a storage 220, and a communication interface 230. The impedance measurer 100 and the processor 200 are described in detail above with reference to FIGS. 1 and 4 to 6, such that description thereof will be omitted.

The output interface 210 may provide processing results of the processor 200 for a user. For example, the output interface 210 may visually output the processing results through a visual display module such as a display and the like. The output interface 210 may divide a display area into two or more areas, and may output basic information, such as impedance information used for analyzing a component, in a first area. Along with the basic information, the output interface 210 may output a component analysis result, e.g., an estimated blood glucose value, in a second area. Further, the output interface 210 may also output component analysis history data during a predetermined period of time in the form of graphs in the second area. In the case where a user selects an analysis result of an in vivo component at any one time in a graph, the output interface 210 may output the basic information used for analyzing the in vivo component at the time and/or other detailed additional information in the first area. In this case, if an estimated component value falls outside a normal range, the output interface 210 may provide the user with information, indicating that the estimated value is abnormal, by highlighting an abnormal value in red and the like or by displaying the abnormal value along with a normal range.

In another example, the output interface 210 may output the analysis result of the in vivo component in a non-visual manner by voice, vibrations, tactile sensation, and the like using an audio output module, such as a speaker, or a haptic module, either alone or in combination with a visual display of an analysis result.

The storage 220 may store a variety of reference information for component analysis, an impedance measurement result, a component analysis result, and the like. In this case, the reference information may include user characteristic information such as a user's age, sex, health condition, and the like, as well as drive current electrodes for component analysis, voltage electrodes, separate current electrodes for monitoring a contact state, time intervals and number of times of impedance measurement for monitoring a contact state, a component analysis model, and the like.

The storage 220 may include at least one storage medium of a flash memory type memory, a hard disk type memory, a multimedia card micro type memory, a card type memory (e.g., a secure digital (SD) memory, an extreme digital (XD) memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

The communication interface 230 may communicate with an external device to transmit and receive various data related to component analysis. The external device may include an information processing device such as a smartphone, a tablet PC, a desktop computer, a laptop computer, and the like.

The communication interface 230 may communicate with the external device by using various wired or wireless communication techniques such as Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, Wi-Fi communication, Radio Frequency Identification (RFID) communication, third generation (3G), fourth generation (4G), and fifth generation (5G) communications, and the like. However, this is merely exemplary and is not intended to be limiting.

Figure 7:
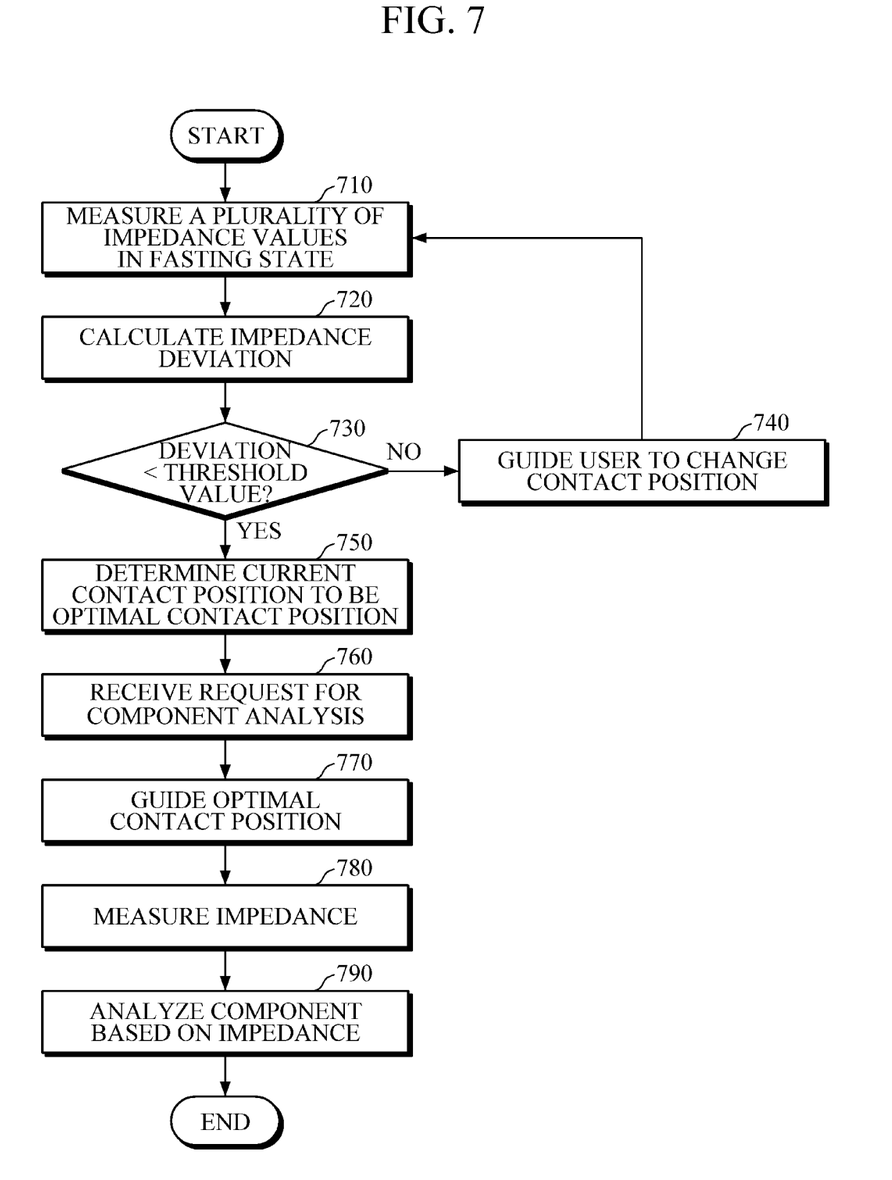
FIG. 7 is a flowchart illustrating a component analyzing method according to an example embodiment.

FIG. 7 is a flowchart illustrating a component analyzing method according to an example embodiment. The component analyzing method of FIG. 7 may be performed by the component analyzing apparatus 1 described above.

The component analyzing apparatus 1 may measure a plurality of impedance values for monitoring a contact state between electrodes and an object while a user is in a fasting state in 710. For example, the component analyzing apparatus 1 may measure the impedance values a predetermined number of times (e.g., three times) at predetermined time intervals (e.g., 15 minutes). In this case, as described above, by sharing current electrodes and voltage electrodes defined for component analysis, the component analyzing apparatus 1 may measure the impedance values for monitoring a contact state. Alternatively, by using separate current electrodes defined for monitoring a contact state, and voltage electrodes defined for component analysis, the component analyzing apparatus 1 may measure the impedance values for monitoring a contact state.

Then, the component analyzing apparatus 1 may calculate a deviation between the measured plurality of impedance values in 720, and may compare the calculated deviation with a predetermined threshold value in 730.

Subsequently, upon comparison, if the deviation is greater than or equal to the predetermined threshold value, the component analyzing apparatus 1 may determine that the contact state is not normal, and may guide a user to change a contact position in 740. In this case, the component analyzing apparatus 1 may visually display a marker, e.g., dot, circle, polygon, cross mark, and the like, which indicates a current position and a position to be changed. Further, the component analyzing apparatus 1 may output a marker, e.g., arrow, for guiding a change from the current position to the position to be changed.

Next, once the user changes the contact position, the component analyzing apparatus 1 may move to the operation 710.

Upon comparison in 730, if the deviation is less than the threshold value, the component analyzing apparatus 1 may determine that the contact state is normal, and may determine the current contact position to be an optimal contact position in 750. In this case, the determined optimal position may be stored in a storage.

Then, upon receiving a request for component analysis in 760, the component analyzing apparatus 1 may provide guide information on the optimal contact position stored in the storage in 770. In this case, the component analyzing apparatus 1 may visually output images of a shape of an object, an arrangement of an electrode part, an arrangement of the drive electrodes, and the like, so as to guide the object to contact in an accurate position.

Subsequently, the component analyzing apparatus 1 may measure impedance for component analysis in 780, and may analyze a component based on the measured impedance in 790. The component analyzing apparatus 1 may output a component analysis result as visual information or non-visual information using voice and the like.

Figure 8:
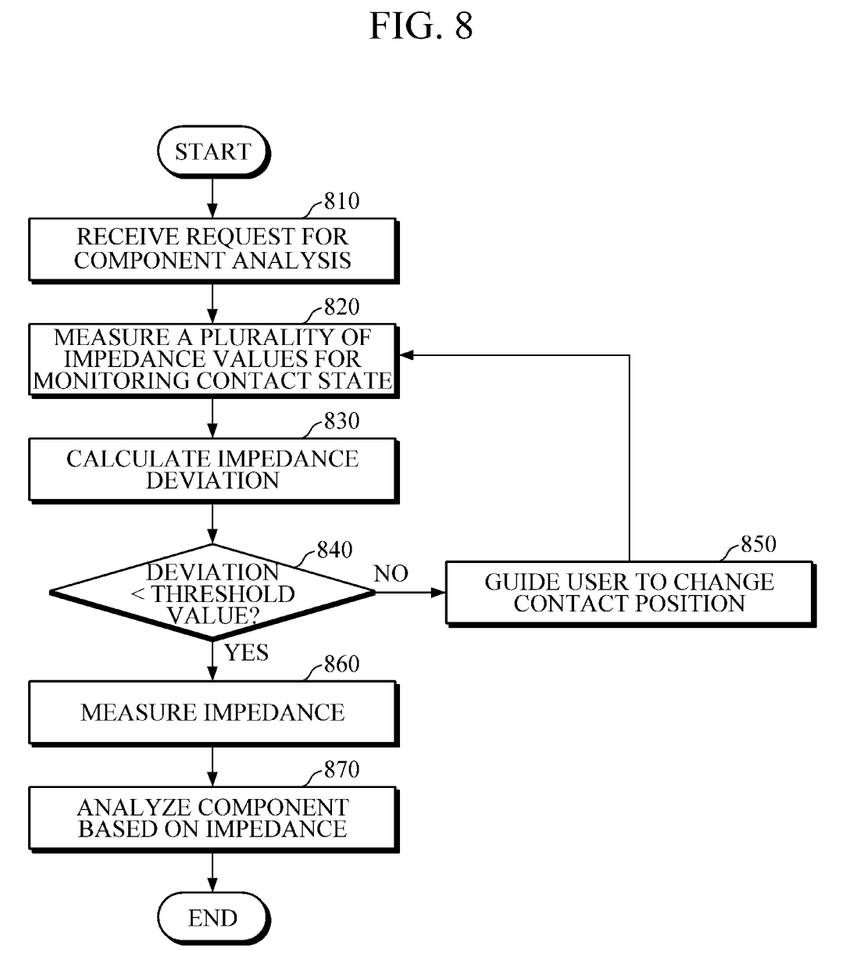
FIG. 8 is a flowchart illustrating a component analyzing method according to another embodiment.

FIG. 8 is a flowchart illustrating a component analyzing method according to another example embodiment. The component analyzing method of FIG. 8 may be performed by any one of the component analyzing apparatus 1 according to the example embodiments of FIG. 1 or FIG. 2, which is described above in detail, and thus will be briefly described below in order to avoid redundancy.

Upon receiving a request for component analysis in 810, the component analyzing apparatus 1 may measure a plurality of impedance values for monitoring a contact state between electrodes and an object before analyzing a component in 820.

Then, the component analyzing apparatus 1 may calculate a deviation between the measured plurality of impedance values in 830, and may compare the calculated deviation with a predetermined threshold value in 840.

Subsequently, upon comparison, if the deviation is greater than or equal to the threshold value, the component analyzing apparatus 1 may determine that the contact state is not normal, and may guide a user to change a contact position in 850. Next, once the user changes the contact position, the component analyzing apparatus 1 may move to the operation 820.

Upon comparison in 840, if the deviation is less than the threshold value, the component analyzing apparatus 1 may determine that the contact state is normal, and may measure impedance for component analysis in 860.

Then, the component analyzing apparatus 1 may analyze a component based on the measured impedance in 870.

Figure 9:
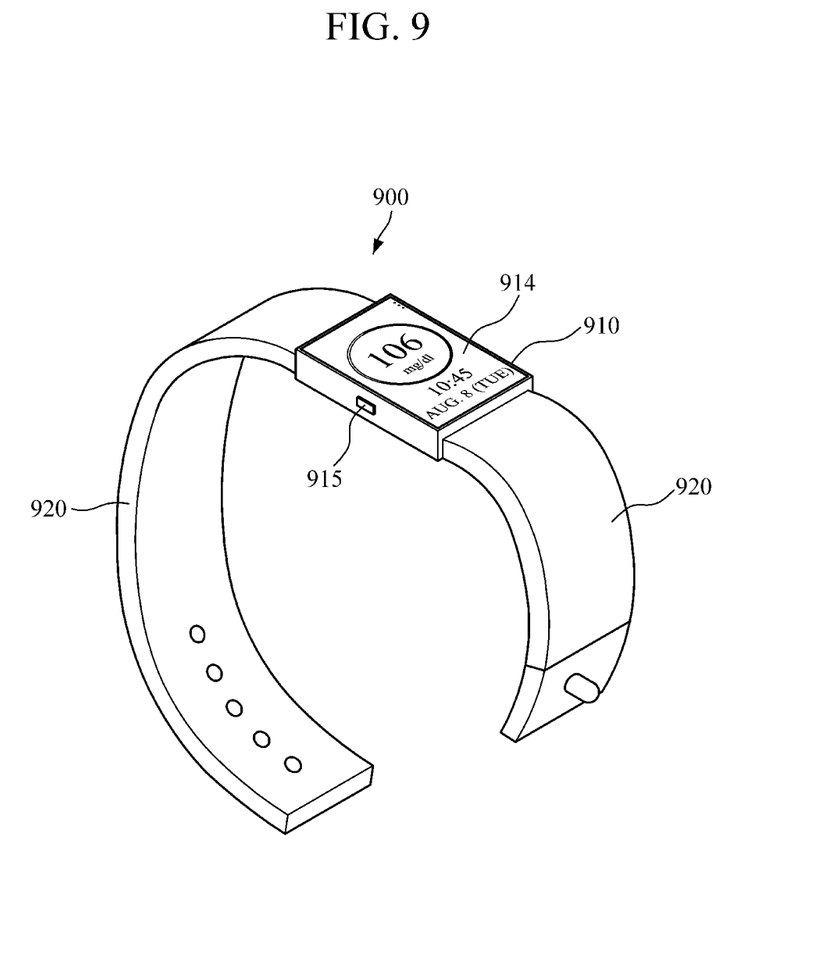
FIG. 9 is a diagram illustrating a wearable device according to an example embodiment.

FIG. 9 is a diagram illustrating a wearable device according to an example embodiment.

FIG. 9 illustrates a wearable device, such as a smart watch to be worn on a user's wrist or a smart band, and the component analyzing apparatus 1 of FIG. 1 or FIG. 2 may be mounted therein.

Referring to FIG. 9, the wearable device 900 includes a main body 910 and a strap 920. Various modules of the component analyzing apparatus 1 of FIG. 1 or FIG. 2 may be embedded in the main body 910.

The main body 910 may be worn on a user's wrist by the strap 920, and the strap 920 may be connected to both sides of the main body 910 so that both ends of the strap 920 may be fastened to each other. The strap 920 may be made of a flexible material to allow the main body 910 to be wrapped around the user's wrist.

A battery, which supplies power to the wearable device 900, may be embedded in the main body 910 or the strap 920.

The main body 910 may include an impedance measurer for obtaining an impedance spectrum from the user's wrist. The impedance measurer may include an electrode part having a plurality of electrodes arranged in a predetermined shape, and an electrode controller for controlling the electrodes of the electrode part.

The electrode part of the impedance measurer may have a compact structure by considering the size of a smart watch, and may be manufactured to have an optimal electrode width by considering an effective measurement depth for analyzing a component of an analyte, e.g., blood glucose component, and an electrode gap according to the compact structure.

The main body 910 may include a camera module, which may obtain an image of an object when the object comes into contact with the main body 910.

A processor, mounted in the main body 910, may be electrically connected to various modules, may control the various modules, and may process information collected therefrom. For example, upon receiving an image of the object from the camera module, the processor may guide a contact position, a contact state, and the like for a user.

The processor may monitor a contact state in a fasting state or when analyzing a component. For example, by sharing current electrodes for estimating a component or by using separate electrodes having a narrower gap than the current electrodes for estimating a component, the processor may measure a plurality of impedance values at predetermined time intervals, and may monitor a contact state by obtaining a deviation between the measured impedance values and by comparing the calculated deviation with a predetermined threshold value. Based on the monitoring result, the processor may obtain an estimated component value by using an impedance value measured in a contact position of a good contact state.

The processor may output guide information for changing the contact position or a component analysis result for a user through a display 914. The display 914 may be mounted at the top of the main body 910, and may output a variety of information under the control of the processor. Further, the display 914 may include a touch screen for receiving a touch input, and may transmit a user's touch input to the processor.

A communication interface may be mounted in the main body 910, and may communicate with an external device. The communication interface may transmit the component analysis result to the external device, so that the external device may perform various functions related to monitoring of a user's health condition. The external device may be an information processing device, such as a smartphone, a tablet PC, a desktop computer, a laptop computer, and the like, which has relatively high computing performance.

The wearable device 900 may further include a manipulator 915 mounted in the main body 910. The manipulator 915 may be mounted on one side of the main body 910 to be exposed to the outside, and may receive an instruction input by a user and transmit the received instruction to the processor. The manipulator 915 may include a function to power on/off the wearable device 900.

The disclosure may be implemented as a computer-readable code written on a computer-readable recording medium. The computer-readable recording medium may be any type of recording device in which data is stored in a computer-readable manner.

Examples of the computer-readable recording medium include a ROM, a RAM, a CD-ROM, a magnetic tape, a floppy disc, an optical data storage, and a carrier wave (e.g., data transmission through the Internet). The computer-readable recording medium can be distributed over a plurality of computer systems connected to a network so that a computer-readable code is written thereto and executed therefrom in a decentralized manner. Functional programs, codes, and code segments needed for implementing the disclosure may be readily deduced by a person of ordinary skill in the art.

Although a few example embodiments have been shown and described, it would be appreciated by those skilled in the art that changes may be made in example embodiments without departing from the principles and spirit of the disclosure, the scope of which is defined in the claims and their equivalents.

What is claimed is:

1. A component analyzing apparatus comprising:
an impedance measurer comprising:
a plurality of electrodes having an electrode width that is determined based on both a desired effective measurement depth for analyzing a component of an analyte and a gap between two adjacent electrodes among the plurality of electrodes, and
an electrode controller configured to select a first electrode and a second electrode among the plurality of electrodes, apply a first current to the first electrode and the second electrode, and to measure impedance based on a voltage between a third electrode and a fourth electrode; and
a processor configured to analyze the component of the analyte based on the impedance measured by the electrode controller.

2. The component analyzing apparatus of claim 1, wherein the plurality of electrodes are arranged in a Wenner array or in a Wenner-Schlumberger array.

3. The component analyzing apparatus of claim 1, wherein the plurality of electrodes are arranged in a Wenner array, and the electrode width has a value according to a model that defines a correlation between a ratio between an electrode width and the gap of the two adjacent electrodes, and an effective measurement depth.

4. The component analyzing apparatus of claim 1, wherein the plurality of electrodes are arranged in a Wenner-Schlumberger array, and the electrode width has a value according to a model that defines a correlation between a ratio between an electrode width and a separation factor, and an effective measurement depth.

5. The component analyzing apparatus of claim 1, wherein the analyte comprises dermis of an object.

6. The component analyzing apparatus of claim 1, wherein the processor is further configured to:
control the electrode controller to monitor a contact state at a contact position between the plurality of electrodes and an object by measuring, in a fasting state of a user, a plurality of impedance values in the contact state, and
obtain an impedance deviation based on the measured plurality of impedance values, and determine whether the contact state at the contact position is normal based on the impedance deviation and a predetermined threshold value.

7. The component analyzing apparatus of claim 6, wherein the processor is further configured to:
provide information to the user to change the contact position based on the impedance deviation being greater than the predetermined threshold value.

8. The component analyzing apparatus of claim 6, wherein the processor is further configured to, based on a request for component analysis, provide information on the contact position corresponding to the contact state that is determined as normal.

9. The component analyzing apparatus of claim 6, wherein the processor is further configured to control the electrode controller to apply a second current to a fifth electrode and a sixth electrode among the plurality of electrodes, and measure the plurality of impedance values by measuring voltages between the third electrode and the fourth electrode.

10. The component analyzing apparatus of claim 9, wherein a gap between the fifth electrode and the sixth electrode is narrower than a gap between the first electrode and the second electrode.

11. The component analyzing apparatus of claim 9, wherein the gap between the fifth electrode and the sixth electrode is within a predetermined multiple of a gap between the third electrode and the fourth electrode.

12. The component analyzing apparatus of claim 6, wherein the processor is further configured to control the electrode controller to monitor the contact state by applying a third current to the first electrode and the second electrode, and measuring the plurality of impedance values based on voltages between the third electrode and the fourth electrode.

13. The component analyzing apparatus of claim 1, wherein the processor is further configured to, based on a request for component analysis, control the electrode controller to monitor a contact state between the plurality of electrodes and an object by measuring a plurality of impedance values, and measure the impedance for component analysis based on the monitored contact state being normal.

14. The component analyzing apparatus of claim 1, wherein the component of the analyte comprises at least one of blood glucose, cholesterol, triglyceride, protein, intracellular water, extracellular water, body water, and uric acid.

15. A component analyzing method comprising:
selecting a first electrode and a second electrode among a plurality of electrodes, wherein the plurality of electrodes have an electrode width that is determined based on both a desired effective measurement depth for analyzing a component of an analyte and a gap between two adjacent electrodes among the plurality of electrodes;
applying a first current to the first electrode and the second electrode;
measuring impedance based on a voltage between a third electrode and a fourth electrode among the plurality of electrodes; and analyzing the component of the analyte based on the impedance that is measured.

16. The component analyzing method of claim 15, wherein the analyte comprises dermis of an object.

17. The component analyzing method of claim 15, further comprising:
monitoring a contact state at a contact position between the plurality of electrodes and an object by measuring, in a fasting state of a user, a plurality of impedance values in the contact state; and
obtaining an impedance deviation based on the measured plurality of impedance values, and determining whether the contact state at the contact position is normal based on the impedance deviation and a predetermined threshold value.

18. The component analyzing method of claim 17, further comprising:
providing information to the user to change the contact position based on the impedance deviation being greater than the predetermined threshold value.

19. The component analyzing method of claim 17, further comprising, based on a request for component analysis, providing information on the contact position corresponding to the contact state that is determined as normal.

20. The component analyzing method of claim 17, wherein the monitoring comprises:
applying a second current to a fifth electrode and a sixth electrode among the plurality of electrodes; and
measuring the plurality of impedance values based on voltages between the third electrode and the fourth electrode.

21. The component analyzing method of claim 20, wherein a gap between the fifth electrode and the sixth electrode is narrower than a gap between the first electrode and the second electrode.

22. The component analyzing method of claim 17, wherein the monitoring comprises:
applying a third current to the first electrode and the second electrode; and
measuring the plurality of impedance values by based on voltages between the third electrode and the fourth electrode.

23. An impedance measuring apparatus comprising:
a plurality of electrodes having an electrode width that is determined based on both a desired effective measurement depth for analyzing a component of an analyte and a gap between two adjacent electrodes among the plurality of electrodes; and
an electrode controller configured to:
select a first electrode and a second electrode among the plurality of electrodes;
apply a first current to the first electrode and the second electrode; and
measure impedance at the desired effective measurement depth based on a voltage between a third electrode and a fourth electrode.

24. The impedance measuring apparatus of claim 23, wherein the electrode controller is further configured to determine the electrode width by using a model that defines a correlation between the gap between the two adjacent electrodes, an electrode width, and an effective measurement depth.

* * * * *